United States Patent [19]

Bernstein

[11] Patent Number: 4,997,853

[45] Date of Patent: Mar. 5, 1991

[54] METHOD AND COMPOSITIONS UTILIZING CAPSAICIN AS AN EXTERNAL ANALGESIC

[75] Inventor: Joel E. Bernstein, Deerfield, Ill.

[73] Assignee: Galenpharma, Inc., Northbrook, Ill.

[21] Appl. No.: 501,424

[22] Filed: Mar. 28, 1990

Related U.S. Application Data

[63] Continuation of Ser. No. 279,587, Dec. 2, 1988, abandoned.

[51] Int. Cl.$^5$ ............................................. A61K 31/16
[52] U.S. Cl. ...................................... 514/626; 514/627
[58] Field of Search ................................. 514/626, 627

[56] References Cited

U.S. PATENT DOCUMENTS 4,536,404 8/1985 Bernstein ........................... 514/627
4,599,342 7/1986 LaHann ............................. 514/627
4,628,063 12/1986 Haines .............................. 514/626
4,681,897 7/1987 Brand ............................... 514/627

*Primary Examiner*—Stanley J. Friedman
*Attorney, Agent, or Firm*—Jones, Day, Reavis & Pogue

[57] ABSTRACT

A method and composition for treating superficial pain syndromes incorporates capsaicin in a therapeutically effective amount into a pharmaceutically acceptable carrier and adding to this composition a local anesthetic such as lidocaine or benzocaine. The composition containing the anesthetic is then applied to the site of the pain. A variation on the treatment includes initial treatment with the composition containing the local anesthetic until the patient has become desensitized to the presence of capsaicin and subsequent treatment with a composition ommitting the local anesthetic.

7 Claims, No Drawings

METHOD AND COMPOSITIONS UTILIZING CAPSAICIN AS AN EXTERNAL ANALGESIC

This application is a continuation of application Ser. No. 279,587 filed Dec. 12, 1988, now abandoned.

BACKGROUND OF THE INVENTION

This invention relates generally to the treatment of superficial pain syndromes and, in particular, to improved uses of capsaicin to treat these conditions. Over the past 5 years topical capsaicin has emerged as the treatment of choice for superficial pain syndromes such as postherpetic neuralgia. See, for example, U.S. Pat. No. 4,536,404 entitled "Method and Composition for Treating Post-Herpetic Neuralgia", issued Aug. 20, 1985 to the inventor named herein. However, from 10% to 30% of patients treated with topical capsaicin experience moderate to severe local reactions, principally stinging or burning of the skin on initial applications. After a period of use, these reactions seem to fade. However, such burning may cause some of these patients to discontinue capsaicin use before they can experience pain relief from the treatment.

It has been discovered that incorporating topical anesthetics such as lidocaine (Entry 5310, p. 786, *Merck Index*, Tenth Edition 1983) and benzocaine (ethyl aminobenzoate, Entry 3710, p. 546, *Merck Index*, Tenth Edition 1983; into formulations containing capsaicin and then applying such formulations for the initial period of treatment can reduce or even eliminate the painful burning from the application of capsaicin, allowing the patient to continue therapy thereafter without requiring the use of anesthetics.

BRIEF DESCRIPTION OF THE INVENTION

In the practice of this invention topical anesthetics such as lidocaine and benzocaine in concentrations from 0.5% to 25% by weight are incorporated into pharmaceutically acceptable carriers such as creams, lotions, gels, ointments, suspensions and solutions containing capsaicin in a concentration of from about 0.01% to about 1% by weight and the resulting formulations are applied 2-6 times daily to the skin of patients with superficial pain disorders. In such a manner, the burning or stinging side effect of capsaicin therapy is reduced from a 10% to 30% incidence to an incidence level of less than 5%. Once the patient has become "desensitized" to the capsaicin, further therapy may be conducted by using the composition without the anesthetic.

DETAILED DESCRIPTON OF THE INVENTION

The following examples demonstrate the invention.

EXAMPLE 1

A cream containing 0.075% capsaicin was applied to the right flexor forearm of a patient four times over a 24 hour period. To the left flexor forearm of the same patient, a cream containing 0.075% capsaicin and 10% lidocaine was applied four times over the test period. The right arm became red and painful immediately at the site of application, and this burning pain decreased only slightly over the 24 hours of application. The left arm also became red at the application site, but only a slight stinging sensation was experienced at the application site on this arm, and after 24 hours no pain was experienced in the left arm.

EXAMPLE 2

A cream containing 0.025% capsaicin was applied to a single site on the right flexor forearm of a patient four times daily for 2 days. The left flexor forearm was treated in a similar fashion, but here a cream containing 0.025% capsaicin and 20% benzocaine was utilized. Intense burning pain was experienced immediately after cream applications to the right arm over the two days, but only moderate pain was experienced in the left arm on the first day and only slight pain in this arm on the second day.

While the foregoing describes the invention within the context of specific, preferred embodiments, it is to be understood that these embodiments, have been presented as example only and are not intended to limit the scope of the present invention. It is expected that others will perceive variations which, while differing from the foregoing, do not depart from the spirit and scope of the invention as herein described and claimed.

What is claimed is:

1. A method for treating superficial pain syndromes, said method comprising the step of topically applying to a patient having superficial pain, an effective amount of a composition comprising a therapeutically acceptable carrier and capsaicin, said capsaicin being present in a concentration, by weight, from about 0.01% to about 1.0%, said composition also including a topical anesthetic in a therapeutically effective amount, said anesthetic being present primarily to inhibit the local topical irritant effect of said capsaicin and whereby said capsaicin provides the primary relief for the pain syndrome.

2. The method of claim 1, wherein said topical anesthetic is lidocaine.

3. The method of claim 1 wherein said topical anesthetic is benzocaine.

4. The method of claim 1 including the further steps of:
   (b) repeating the application of the composition until the capsaicin no longer produces an irritating or painful reaction; and
   (c) applying subsequent applications of a composition containing only the therapeutically acceptable carrier and capsaicin and without any anesthetic.

5. A topical composition for the treatment of superficial pain syndromes, said composition comprising a therapeutically acceptable carrier, capsaicin in an amount of from about 0.01 to 1.0% by weight, and a topical anesthetic in a therapeutically effective amount, said anesthetic being present primarily to inhibit the local topical irritant effect of said capsaicin when the composition is applied to a patient, whereby said capsaicin provides the primary relief of the pain syndrome.

6. The composition of claim 5, wherein said topical anesthetic is selected from the group consisting of lidocaine and benzocaine.

7. The composition of claim 6 wherein said topical anesthetic is present in a concentration from about 0.5% to about 25.0% by weight.

* * * * *